United States Patent
Huang et al.

(10) Patent No.: US 10,918,558 B2
(45) Date of Patent: Feb. 16, 2021

(54) PORTABLE HUMAN EXOSKELETON SYSTEM

(71) Applicant: iMobilities Incorporated, Yunlin County (TW)

(72) Inventors: Chen-Ming Huang, Kaohsiung (TW); Yen-Chieh Mao, Yunlin County (TW)

(*) Notice: Subject to any disclaimer, the term of this patent is extended or adjusted under 35 U.S.C. 154(b) by 1163 days.

(21) Appl. No.: 15/019,446

(22) Filed: Feb. 9, 2016

(65) Prior Publication Data
US 2016/0158087 A1    Jun. 9, 2016

Related U.S. Application Data

(63) Continuation of application No. PCT/CN2014/084000, filed on Aug. 8, 2014.
(Continued)

(51) Int. Cl.
*A61H 3/00* (2006.01)
*A61H 1/02* (2006.01)
*A61F 2/60* (2006.01)

(52) U.S. Cl.
CPC .............. *A61H 3/00* (2013.01); *A61F 2/60* (2013.01); *A61H 1/024* (2013.01); *A61H 1/0244* (2013.01);
(Continued)

(58) Field of Classification Search
CPC combination set(s) only.
See application file for complete search history.

(56) References Cited

U.S. PATENT DOCUMENTS

| 5,016,869 A | 5/1991 | Dick et al. |
| 5,230,697 A | 7/1993 | Castillo et al. |

(Continued)

FOREIGN PATENT DOCUMENTS

| CN | 1872016 A | 12/2006 |
| CN | 101103949 A | 1/2008 |

(Continued)

OTHER PUBLICATIONS

A. E. Barr, K. L. Siegel, J. V. Danoff, C.L. McGawey III, A. Tomasko, I. Sable, S.J. Stanhope, "Biomechanical Comparison of the Energy-Storing Capabilities of SACH and Carbon Copy II Prostheitc Feet During the Stance Phase of Gait in a Person with Below-Knee Amputation", Physical Therapy, vol. 72, No. 5, 1992, pp. 344-354.

(Continued)

*Primary Examiner* — Christopher D. Prone

(57) ABSTRACT

A portable human exoskeleton system includes a pelvis module, a leg module and a foot module. The pelvis module includes a bendable member and a pelvis module connector. The foot module includes a foot module connector. The leg module includes: a femur module detachably coupled to the pelvis module connector; a tibia module detachably coupled to the foot module connector; and a knee joint component having at least two linkages with different lengths wherein each linkage is pivotally coupled to the femur module and the tibia module. Weight above the hip of the user is exerted on the pelvis module, and transferred to the leg module and the foot module. The exoskeleton system is easily disassembled and carried, and can be worn inside attire without affecting appearance of the user.

9 Claims, 11 Drawing Sheets

Related U.S. Application Data

(60) Provisional application No. 61/864,529, filed on Aug. 10, 2013.

(52) U.S. Cl.
CPC .. *A61H 2003/001* (2013.01); *A61H 2003/002* (2013.01); *A61H 2201/0165* (2013.01); *A61H 2201/1246* (2013.01); *A61H 2201/1261* (2013.01); *A61H 2201/1436* (2013.01); *A61H 2201/163* (2013.01); *A61H 2201/164* (2013.01); *A61H 2201/165* (2013.01); *A61H 2201/1628* (2013.01); *A61H 2201/1642* (2013.01); *A61H 2201/1652* (2013.01)

(56) References Cited

U.S. PATENT DOCUMENTS

| | | |
|---|---|---|
| 5,458,656 A | 10/1995 | Phillips |
| 5,766,140 A | 6/1998 | Tillinghast, III et al. |
| 5,961,556 A | 10/1999 | Thorn |
| 6,007,582 A | 12/1999 | May |
| 6,610,101 B2 | 8/2003 | Herr et al. |
| 6,764,520 B2 | 7/2004 | Deffenbaugh et al. |
| 6,852,131 B1 | 2/2005 | Chen et al. |
| 7,198,071 B2 | 4/2007 | Bisbee, III et al. |
| 7,279,009 B2 | 10/2007 | Herr et al. |
| 7,628,766 B1 | 12/2009 | Kazerooni et al. |
| 7,691,154 B2 | 4/2010 | Asgeirsson et al. |
| 7,799,091 B2 | 9/2010 | Herr et al. |
| 7,947,004 B2 | 5/2011 | Kazerooni et al. |
| 2002/0013544 A1 | 1/2002 | Stearns |
| 2004/0064195 A1 | 4/2004 | Herr |
| 2005/0251079 A1 | 11/2005 | Carvey et al. |
| 2006/0136072 A1 | 6/2006 | Bisbee, III et al. |
| 2006/0249315 A1 | 11/2006 | Herr et al. |
| 2006/0276728 A1 | 12/2006 | Ashihara et al. |
| 2007/0004570 A1 | 1/2007 | Afanasenko et al. |
| 2007/0027555 A1 | 2/2007 | Palmer et al. |
| 2007/0043449 A1 | 2/2007 | Herr et al. |
| 2007/0123997 A1 | 5/2007 | Herr et al. |
| 2007/0162152 A1 | 7/2007 | Herr et al. |
| 2007/0233279 A1 | 10/2007 | Kazerooni et al. |
| 2008/0009778 A1 | 1/2008 | Hiki |
| 2008/0114272 A1 | 5/2008 | Herr et al. |
| 2008/0154165 A1* | 6/2008 | Ashihara ................ 602/23 |
| 2008/0161937 A1 | 7/2008 | Sankai |
| 2008/0255670 A1 | 10/2008 | Boiten et al. |
| 2008/0300692 A1 | 12/2008 | Moser et al. |
| 2009/0014042 A1 | 1/2009 | Ashihara et al. |
| 2009/0036815 A1 | 2/2009 | Ido |
| 2009/0306554 A1 | 12/2009 | Yasuie |
| 2010/0010639 A1 | 1/2010 | Ikeuchi |
| 2010/0076360 A1* | 3/2010 | Shimada .............. A61B 5/1038 602/23 |
| 2010/0113986 A1 | 5/2010 | Ashihara et al. |
| 2010/0138000 A1 | 6/2010 | Palmer et al. |
| 2010/0198116 A1 | 8/2010 | Hirata et al. |
| 2010/0241242 A1 | 9/2010 | Herr et al. |
| 2010/0298746 A1 | 11/2010 | Shimizu et al. |
| 2011/0040216 A1 | 2/2011 | Herr et al. |

FOREIGN PATENT DOCUMENTS

| | | |
|---|---|---|
| CN | 201375624 Y | 1/2010 |
| CN | 201431599 Y | 3/2010 |
| CN | 202526510 U | 11/2012 |
| CN | 102871822 A | 1/2013 |
| CN | 202761650 U | 3/2013 |
| JP | 2013138784 | 7/2013 |
| TW | 478349 U | 3/2002 |
| TW | 478349 U | 3/2002 |
| TW | 201238575 | 10/2012 |
| TW | 201238575 A1 | 10/2012 |
| WO | 0200156 A2 | 1/2002 |
| WO | 2009082249 A2 | 7/2009 |

OTHER PUBLICATIONS

B. S. Farber, J. S. Jacobson, "An above-knee prosthesis with a system of energy recovery: a technical note", Journal of Rehabilitation Research and Development, vol. 32, No. 4, Nov. 1995, pp. 337-348.

Burnaby Orthopaedic & Mastectomy "Generation II Custom Knee Braces", http://www.burnabyorthopaedic.com/, Mar. 23, 2016, Burnaby Orthopaedic & Mastectomy.

Ralph Mosher "G.E. Hardiman I Exoskeleton—Ralph Mosher (American)", 1965, http://cyberneticzoo.com/man-amplifiers/1966-69-g-e-hard.

Andrew Chu, H. Kazerooni, and Adam Zoss, "On the Biomimetic Design of the Berkeley Lower Extremity Exoskeleton (BLEEX)", Proceedings of the 2005 IEEE International Conference on Robotics and Automation, Barcelona, Spain, Apr. 2005, pp. 4356-4363.

Aaron M. Dollar, Hugh Herr, "Lower Extremity Exoskeletons and Active Orthoses: Challenges and State-of-the-Art", IEEE Transactions on Robotics, vol. 24, No. 1, Feb. 2008, pp. 144-158.

Liu, X., et al. "Development of a Lower Extremity Exoskeleton for Human Performance Enhancement.", Proceedings of IEEE/RSJ International Conference on Intelligent Robots and Systems, pp. 3889-3894, Sendai, Japan, Sep. 28-Oct. 2, 2004.

Vukobratovi, M., Borovac, B., Surla, D., Stoki, D., "Biped Locomotion: Dynamics, Stability, Control, and Application", 1990, Scientific Fundamentals of Robotics7, Springer-Verlag Berlin Heidelberg.

Yoshiyuki Sankai, "HAL: Hybrid Assistive Limb based on Cybernics", 2011, Global COE Cybernics, System and Information Engineering University of Tsukuba, Japan.

Jerry E. Pratt, Benjamin T. Krupp, Christopher J. Morse, Steven H. Collins, "The RoboKnee: An Exoskeleton for Enhancing Strength and Endurance During Walking", Proceedings of the 2004 IEEE International Conference on Robotics & Automation, New Orleans, LA, Apr. 2004, pp. 2430-2435.

* cited by examiner

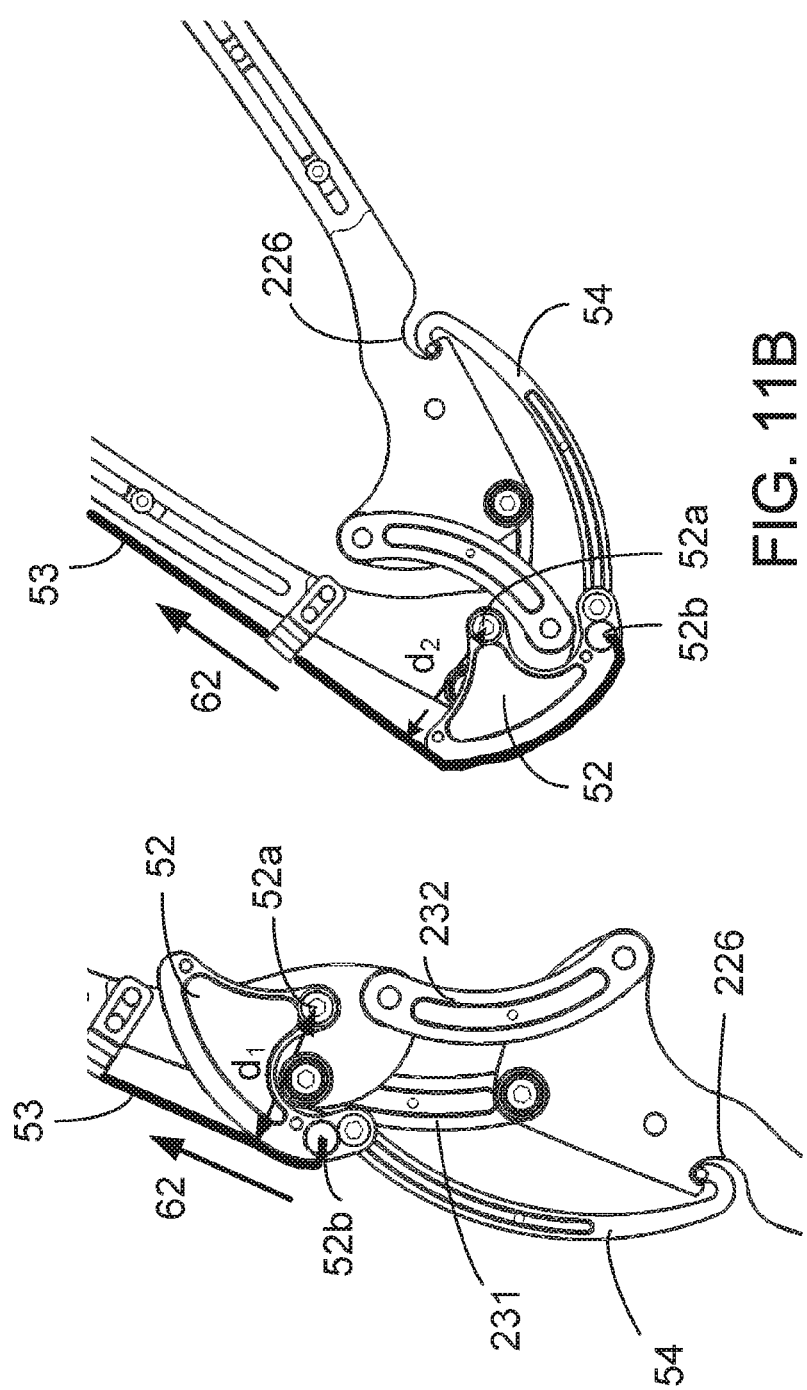

PORTABLE HUMAN EXOSKELETON SYSTEM

CROSS-REFERENCE TO RELATED APPLICATION

This application is a continuation application (CA) application of International (PCT) Patent Application No. PCT/CN2014/084000 filed on Aug. 8, 2014, designating the U.S., which also claims benefit from a US provisional application bearing a Ser. No. 61/864,529 and filed Aug. 10, 2013. The entirety of the above-mentioned patent applications is hereby incorporated by reference herein and made a part of this specification.

FIELD OF THE INVENTION

The present disclosure relates to a human exoskeleton system, and particularly to a portable human exoskeleton system.

BACKGROUND OF THE INVENTION

For a patient or an injured person who can not walk normally or someone who must carry a heavy load in a particular situation, a human exoskeleton system can provide effective assistance. For example, US 2007/0123997 discloses a lower limb exoskeleton system to increase load capacity and reduce possible injury.

The exoskeleton system is mainly designed for supporting loads or a portion of body weight of the user. It should be adaptable to various poses of the human body in motion (e.g. running, walking and squatting). Even additional great power system (e.g. batteries) is required to supply electricity to control actions of each joint. Thus, the bulky and heavy system is not easy to carry, and the user can not put on/take off the system quickly while temporary unloading of the system is desired (e.g. boarding). For the patient or injured person who needs to wear the human exoskeleton system for a long time, quality of life is seriously affected. Therefore, the major objective of the present application is to overcome the drawbacks to provide a human exoskeleton system which can be easily carried, put on and taken off.

SUMMARY OF THE INVENTION

Based on the above drawbacks, the present invention provides a portable human exoskeleton system which is easily disassembled and carried, and can be worn inside attire without affecting appearance of the user.

Another objective is to provide a portable human exoskeleton system which provides an extension moment and/or has a soft pad to properly protect the knee joint. The length of a leg module of the portable human exoskeleton system can be easily adjusted so that the system is rich in practicability.

To achieve the above-mentioned objective, an embodiment of the present invention provides a portable human exoskeleton system, including a pelvis module, a leg module and a foot module. The pelvis module includes: a bendable member around a body of the user to fix the pelvis module to a hip of the user; and a pelvis module connector connected to the bendable member and positioned near a lateral side of a hip joint of the user. The foot module is worn on a foot of the user and has a foot module connector. Furthermore, the leg module is positioned at a lateral side of a leg of the user and includes: a femur module detachably coupled to the pelvis module connector; a tibia module detachably coupled to the foot module connector; and a knee joint component having at least two linkages with different lengths wherein each linkage is pivotally coupled to the femur module and the tibia module. Weight above the hip of the user is exerted on the pelvis module, transferred from the pelvis module to the leg module, and then transferred to the foot module.

Compared to the prior arts, the present invention has advantages that the portable exoskeleton system is easily disassembled and carried, and can be worn inside attire without affecting appearance of the user. Furthermore, an extension moment and/or a soft pad are provided to properly protect the knee joint. The length of the leg module can be easily adjusted so that the system is rich in practicability.

According to the above conception, the bendable member of the pelvis module includes: a groin belt connected to a distal end of the pelvis module connector and going along a lateral side of a pelvis, a groin, an ischium and the lateral side of the pelvis of the user; and a waist belt connected to a proximal end of the pelvis module connector and worn around a waist of the user.

According to the above conception, the bendable member includes: another groin belt; and a tension belt connected between the groin belts behind the hip of the user.

According to the above conception, the foot module includes: a foot frame extending along a lengthwise direction of a foot of the user and positioned at a lateral side of the foot of the user; and at least one support element having a first end and a second end. The first end is connected to the foot frame and the second end extends along a medial direction of the foot of the user.

According to the above conception, the support element is inserted into a sole or an insole of the shoe worn by the user.

According to the above conception, the pelvis module connector includes a first coupling part. The foot module connector is connected to one end of the foot frame. The foot module connector includes a second coupling part. The femur module includes a femur module connector at a proximal end of the femur module. The femur module connector includes a first coupled part to be attached to the first coupling part. The tibia module includes a tibia module connector at a distal end of the tibia module. The tibia module includes a second coupled part to be attached to the second coupling part. The femur module connector and the pelvis module connector form detachable coupling. When the first coupled part is attached to the first coupling part, the femur module is coupled to the pelvis module. When the first coupled part is detached from the first coupling part, the femur module is separated from the pelvis module. The tibia module connector and the foot module connector form detachable coupling. When the second coupled part is attached to the second coupling part, the tibia module is coupled to the foot module. When the second coupled part is detached from the second coupling part, the tibia module is separated from the foot module.

According to the above conception, the first coupled part is attached to the first coupling part by a tenon and mortise structure, a magnetic element, a hook-and-loop fastener or a buckle. The second coupled part is attached to the second coupling part by a tenon and mortise structure, a magnetic element, a hook-and-loop fastener or a buckle.

According to the above conception, the femur module includes: a first linkage having a first curvature fitting a thigh of the user wherein at least one fastening member is provided on the first linkage along a lengthwise direction of the first linkage; and a second linkage having the first curvature and including a slot formed along a lengthwise direction of the second linkage. The fastening member of the first linkage is inserted into the slot at a specific position to fix a relative position of the first linkage and the second linkage.

According to the above conception, the femur module includes a thigh belt fixed to the first linkage or the second linkage. Two ends of the thigh belt have corresponding connection members. The thigh belt is worn around the thigh of the user by connecting the two ends of the thigh belt together.

According to the above conception, the tibia module includes: a third linkage having a second curvature fitting a shank of the user and including a slot formed along a lengthwise direction of the third linkage; and a fourth linkage having the second curvature wherein at least one fastening member is provided on the fourth linkage along a lengthwise direction of the fourth linkage. The fastening member of the fourth linkage is inserted into the slot at a specific position to fix a relative position of the third linkage and the fourth linkage.

According to the above conception, the tibia module includes a shank belt fixed to the third linkage or the fourth linkage. Two ends of the shank belt have corresponding connection members. The shank belt is worn around the shank of the user by connecting the two ends of the shank belt together.

According to the above conception, the portable body exoskeleton system further includes a force transmission device. The force transmission device includes: a moment arm-adjusting structure having a pivot joint pivotally coupled to a distal end of the femur module; and a driving element having a first end and a second end. The first end of the driving element is connected to the pelvis module or the femur module. The second end of the driving element is connected to an input force joint of the moment arm-adjusting structure or the tibia module. The driving element provides a force to urge the femur module and the tibia module toward an extension mode. When the femur module and the tibia module have a first flexion angle, the force corresponds to a first effective moment arm about the pivot joint. When the femur module and the tibia module have a second flexion angle smaller than the first flexion angle, the force corresponds to a second effective moment arm about the pivot joint wherein the first effective moment arm is greater than the second effective moment arm.

According to the above conception, the moment arm-adjusting structure is a cam or an L-shape linkage. The driving element includes a spring, a cable, a cylinder or a combination thereof.

According to the above conception, the driving element is connected to the input force joint of the moment arm-adjusting structure. The force transmission device further includes a hook structure pivotally coupled to the moment arm-adjusting structure. When the hook structure hooks a notch on the tibia module, the force is applied to the tibia module. When the hook structure is detached from the notch, the force is not applied to the tibia module.

According to the above conception, the portable human exoskeleton system further includes a load-carrying module connected to the pelvis module connector of the pelvis module.

According to the above conception, the portable human exoskeleton system further includes:
a groin belt fixed to the femur module;
a shank belt fixed to the tibia module; and
a soft pad fixed to a medial side of the knee joint component and in contact with a lateral side of a knee joint of the user to provide a medial force. The groin belt, the shank belt and the soft pad collectively provide an abduction moment to the knee joint.

BRIEF DESCRIPTION OF THE DRAWINGS

FIG. 11A and FIG. 11B are schematic diagrams showing that the force transmission device controls the knee joint component according to another embodiment of the present invention.

Figure 1:
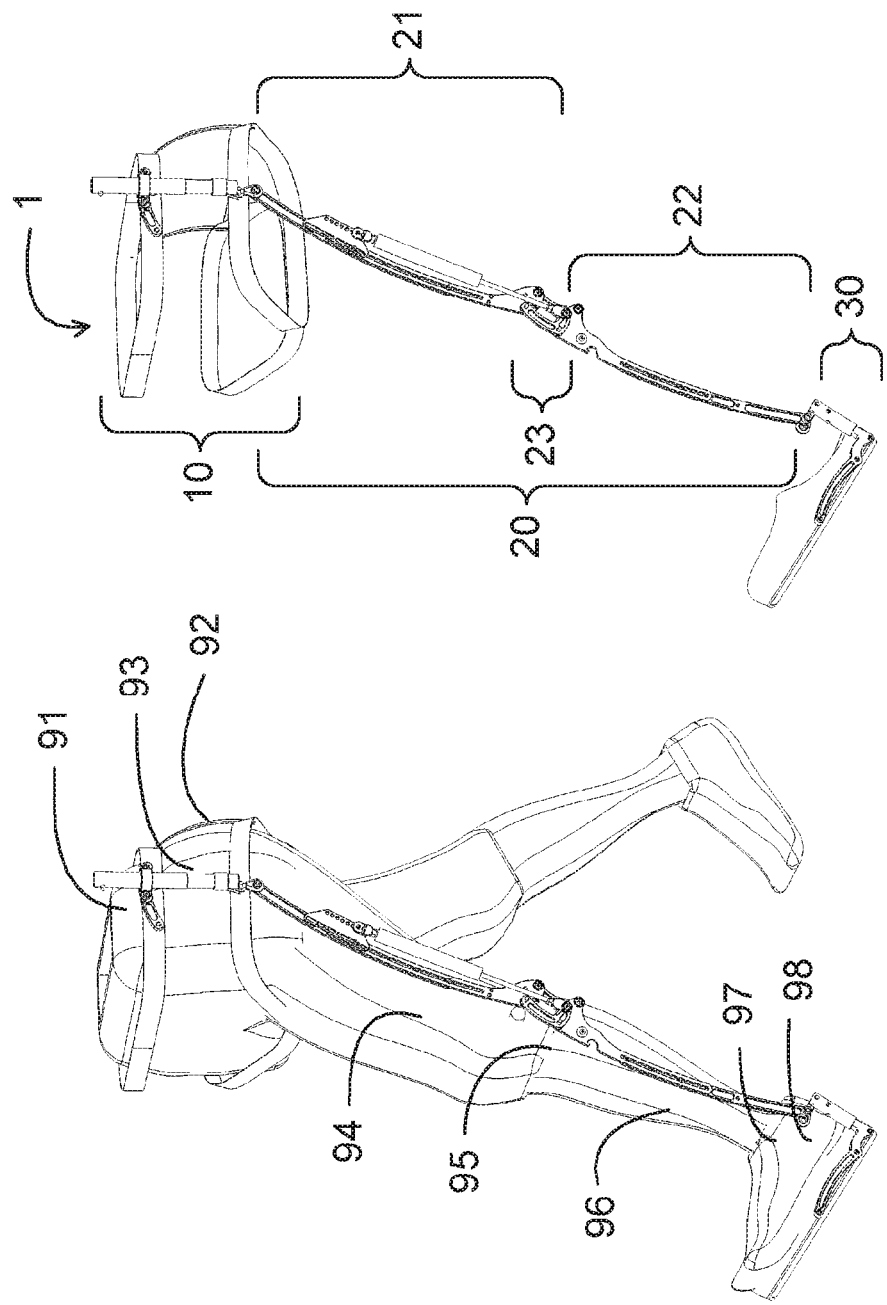
FIG. 1 is a schematic diagram illustrating a portable human exoskeleton system according to an embodiment of the present invention.

The labels are listed as follows:

1 portable human exoskeleton system
10 pelvis module
11 bendable member
12 pelvis module connector
20 leg module
21 femur module
22 tibia module
23 knee joint component
30 foot module
31 foot frame
32 support element
33 foot module connector
40 load-carrying module
41 carry pack
42 support member
43 strap
50 force transmission device
51 cylinder
52 cam
52a pivot joint
52b input force joint
53 driving element
54 hook structure
60 pushing force
62 pulling force
91 waist
92 hip
93 pelvis (hip joint)
94 thigh
95 knee joint
96 shank
97 ankle (ankle joint)
98 foot -continued 111 waist belt
112 groin belt
113 holding belt
114 tension belt
121, 331 coupling part
121a hole
211 femur module connector
212, 213, 221, 222 linkage
214 thigh belt
215 hip joint connector
223 shank belt
224 tibia module connector
225 ankle joint connector
226 notch
231 short linkage (L-shape linkage)
231a, 231b, 231c, 232a, 232b pivot joint
232 short linkage
233 soft pad
2111, 2241 coupled part
2111a button
2121, 2221 fastening member
2131, 2211 slot

DETAILED DESCRIPTION OF PREFERRED EMBODIMENTS

In the biology field, specific terms are used for the human body. For example, "proximal end" refers to one end closer to the heart, "distal end" refers to one end farther from the heart, "medial side" refers to one side closer to the sagittal plane of the human body, and "lateral side" refers to one side farther from the sagittal plane of the human body. These terms are not further explained in the description and the claims of the present invention.

Please refer to FIG. 1, a schematic diagram illustrating a portable human exoskeleton system according to an embodiment of the present invention. The left part is a schematic diagram showing the portable human exoskeleton system worn on a human body. It is mainly used for lower extremity of the human body, involving the waist 91, the hip 92, the pelvis (hip joint) 93, the thigh 94, the knee joint 95, the shank 96, the ankle (ankle joint) 97 and the foot 98. The right part is a simplified drawing of the portable human exoskeleton system 1. Only a left portion is shown in the drawing, but a single right portion or both portions can be designed to meet requirements in practice. Since the structure is substantially identical, only the left portion is described in the specification of the present invention. In this embodiment, the portable human exoskeleton system 1 includes a pelvis module 10, a leg module 20 and a foot module 30. The leg module 20 may include a femur module 21, a tibia module 22 and a knee joint component 23. The structure of each element is described in detail in the following description.

Figure 2:
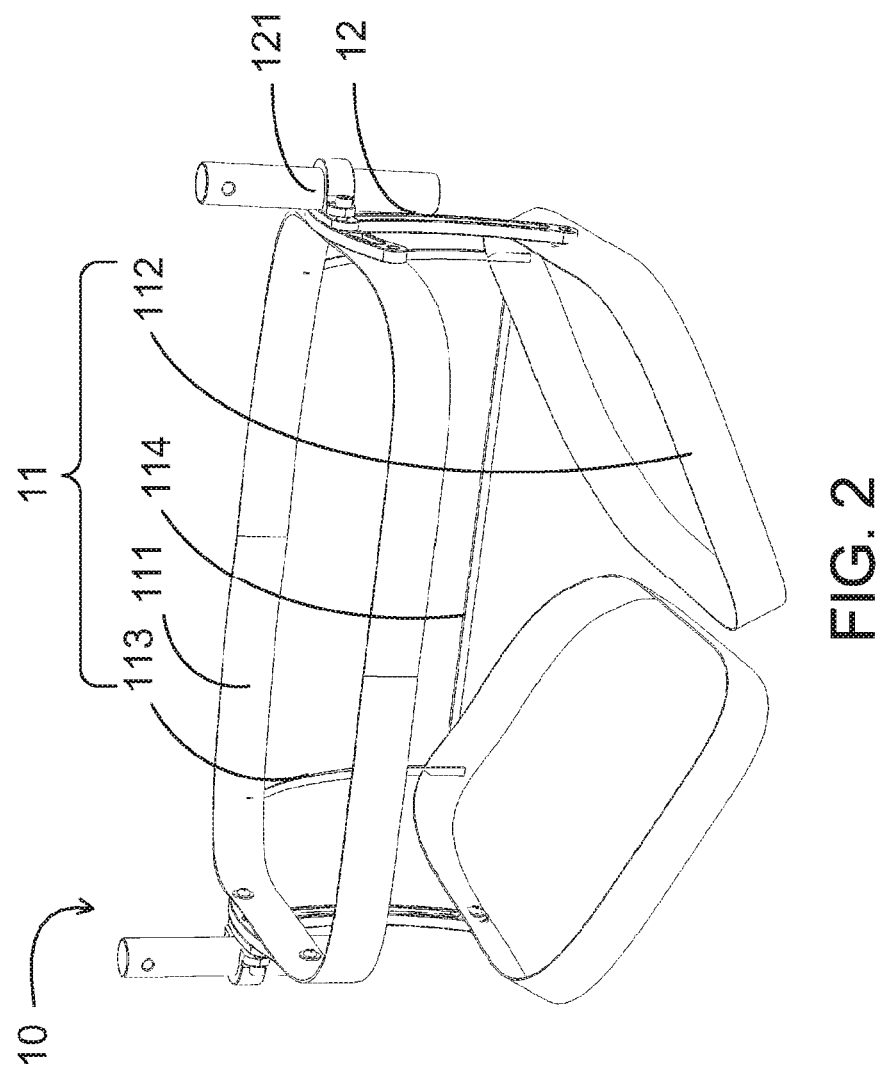
FIG. 2 is a schematic diagram illustrating the pelvis module of FIG. 1.

Please refer to FIG. 2, a schematic diagram illustrating the pelvis module of FIG. 1. The pelvis module 10 includes a bendable member 11 and a pelvis module connector 12. The bendable member 11 is made of a soft material (e.g. cloth, strip with hook-and-loop fasteners, plastic rope or other proper material). The size and the position of the bendable member 11 can be adjusted to fit user body or limbs and worn around the body of the user. Thus, the entire pelvis module 10 can be fixed to the hip 92 of the user. After the user wears the pelvis module 10, the bendable member 11 may be glued to the skin of the user and worn inside the underpants, or the bendable member 11 is worn between the underpants and the pants, or outside the pants. It may be adjusted according to user habit or specific occasion. The pelvis module connector 12 is made of a hard material (e.g. stainless steel, alloy steel, aluminum alloy (aluminum alloy in 4000 series or 7000 series is better, but is not limited thereto), engineering plastics, ABS, carbon fiber, glass fiber or other proper material), and can be connected to the bendable member 11. The pelvis module connector 12 is positioned near the lateral side of the hip joint 93 of the user.

The bendable member 11 mainly includes a waist belt 111 and a groin belt 112, respectively connected to the proximal end and the distal end of the pelvis module connector 12. The waist belt 111 is worn around the waist 91 of the user. The groin belt 112 goes from the lateral side of the pelvis 93, goes along the groin, the ischium and goes back to the lateral side of the pelvis 93. The waist belt 111 and the groin belt 112 may be annular members with fixed shapes. The user puts on/takes off the pelvis module 10 as he or she puts on/takes off pants. Otherwise, two ends of each of the waist belt 111 and the groin belt 112 have corresponding connection members (not shown) by means of, for example, buckling or touch fastening. The two ends are connected together to provide the annular member. Therefore, by disconnecting or connecting the two ends of the waist belt 111/groin belt 112, the user can easily puts on/takes off the pelvis module 10. The user may even adjust the tightness of the waist belt 111 and the groin belt 112 easily to keep the user in comfort.

As shown in FIG. 2, the pelvis module connector 12 has a certain length to space out the waist belt 111 and the groin belt 112 which are respectively connected to the proximal end and the distal end of the pelvis module connector 12. In other applications, the pelvis module connector 12 may be shortened so that the waist belt 111 is close to the groin belt 112 at the lateral side of the pelvis 93, even overlapping the groin belt 112 (not shown). Such applications do not depart from the scope of the present invention.

The bendable member 11 may further include a holding belt 113 to be connected between the waist belt 111 and the groin belt 112 to prevent the groin belt 112 from sliding downwards. It is no necessary to dispose the holding belt 113 behind the human body (as shown in FIG. 2). The holding belt 113 may be disposed in front of the human body (not shown) or a plurality of holding belts 113 are disposed wherein some are behind and others are in front of the human body. It is not necessary to dispose the holding belt 113 near the left side or the right side of the human body, and the holding belt 113 may be disposed near the median of the human body. Therefore, the present invention does not limit the positions of the holding belts 113 relative to the median. The bendable member 11 may further include a tension belt 114 connected between two groin belts 112 or two holding belts 113 behind the hip 92 to prevent the groin belts 112 from sliding along the thigh 94 or limit the sliding range. The tension belt 114 can also prevent the pelvis module connector 12 from moving toward the front and leaving the lateral side of the hip joint 93 due to the force from the femur module 21. The position of the tension belt 114 may be higher than the anus and the urinary meatus or avoid any area which will adversely affect male/female wearer to excrete waste. Therefore, the worn pelvis module 10 will not affect the user to excrete waste (in fact, all belts of the bendable member 11 avoid the relative areas). The above holding belt 113 and tension belt 114 are not necessary for the present invention and may be omitted.

The number of the above-mentioned belts of the bendable member 11 is not limited. For example, the pelvis module 10 of the present invention may include one (left or right) groin belt 112 or two groin belts 112, and may include one or multiple holding belts 113.

The pelvis module connector 12 includes a first coupling part 121. As shown in FIG. 2, the first coupling part 121 is tubular, but is not limited to this shape. The use of the first coupling part 121 together with the femur module 21 will be described later.

According to the design of the pelvis module 10 of the present invention, the bendable member 11 is made of a soft material and can be adjusted according to the figure of the user. Abduction or adduction of the hip joint 93 does not upset the user. Furthermore, the force exerted through the pelvis module connector 12 is transferred to the waist belt 111 and/or the groin belt 112 instead of the human body.

Figure 3:
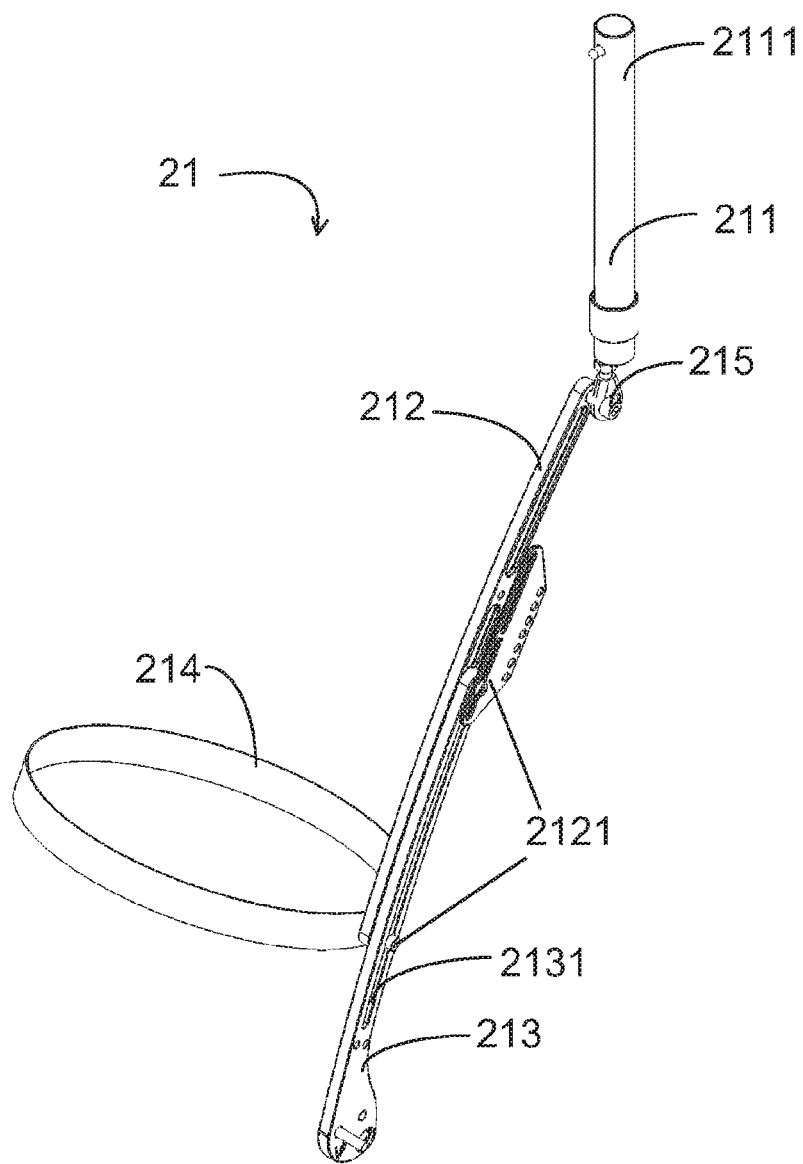
FIG. 3 is a schematic diagram illustrating the femur module of FIG. 1.

Please refer to FIG. 3, a schematic diagram illustrating the femur module of FIG. 1. The femur module 21 includes a femur module connector 211, a first linkage 212, a second linkage 213 and a thigh belt 214.

Figure 4:
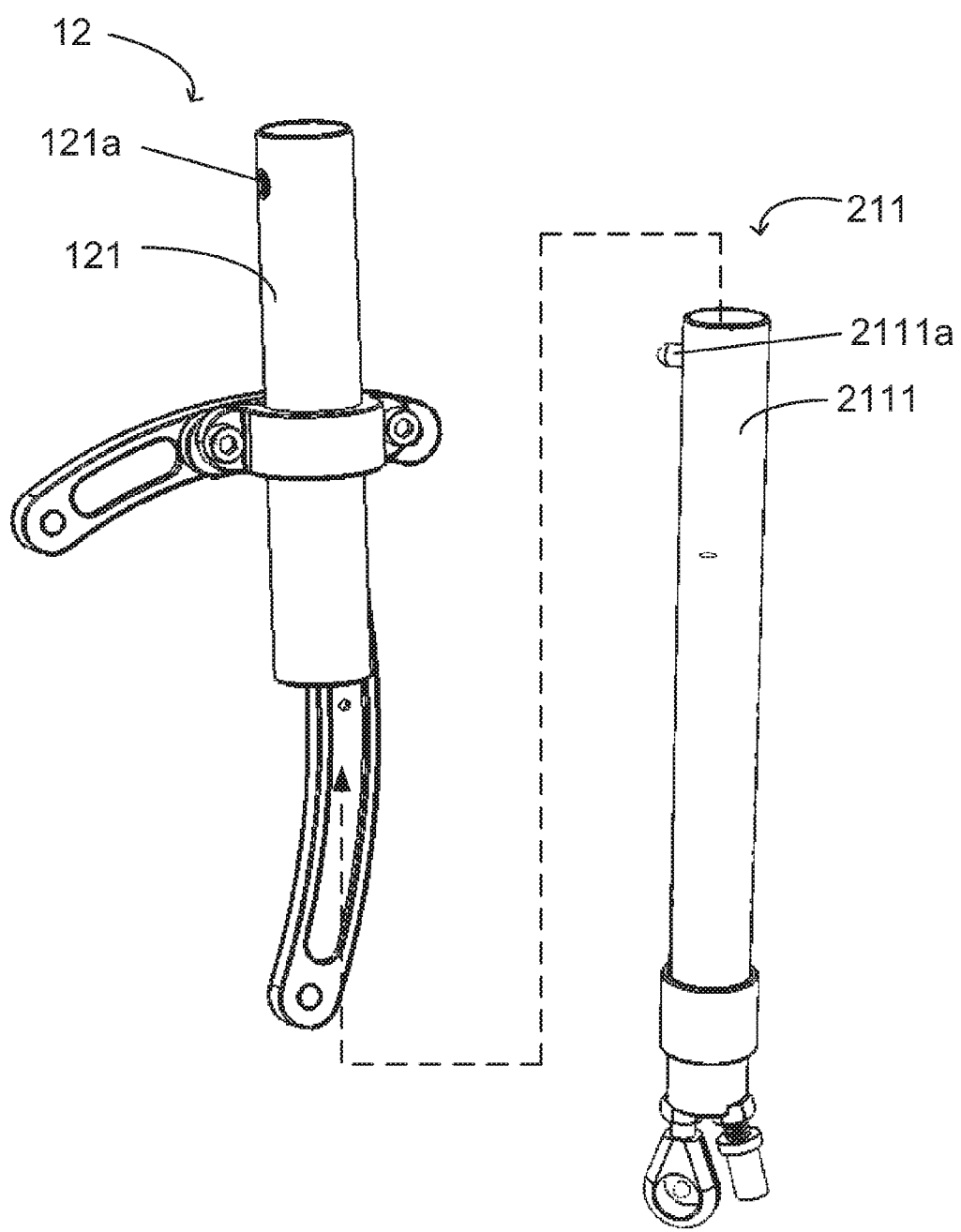
FIG. 4 is a schematic diagram illustrating detachable coupling between the pelvis module connector and the pelvis module connector.

The femur module connector 211 is disposed at the proximal end of the femur module 21 and has a first coupled part 2111 to be attached to the first coupling part 121 of the pelvis module 12 to form detachable coupling. The coupling manner is shown in FIG. 4. One or multiple holes 121a are disposed on the first coupling part 121 of the pelvis module connector 12. One or multiple corresponding buttons 2111a or other elastic members are disposed on the first coupled part 2111 of the femur module connector 211. When the first coupled part 2111 is inserted into the first coupling part 121, the button 2111a protrudes from the hole 121a so that the first coupled part 2111 is fixed in the first coupling part 121. Thus, the femur module 21 is coupled to the pelvis module 10. To detach the first coupling part 121 from the first coupled part 2111, the user presses the button 2111a and pulls the first coupled part 2111 downwards (or toward the front or the lateral side according to the design for specific user). Then, the femur module 21 and the pelvis module 10 are separated. The present invention does not limit the detachable coupling to the embodiment. For example, the detachable coupling may be achieved by a tenon and mortise structure, a magnetic element, a hook-and-loop fastener, a buckle or a combination thereof. Hence, the present invention provides a quick and convenient way of detachment and attachment. Even though the user wears the pelvis module 10, he or she can easily detach or attach the femur module 21 by himself or herself, even by single hand. For example, the left femur module 21 can be equipped or removed only by right hand operation.

Please refer to FIG. 3 again. The first linkage 212 and the second linkage 213 of the femur module 21 have the same curvature fitting the thigh 94 of the user. At least one fastening member 2121, e.g. screw, is provided on the first linkage 212 along a lengthwise direction of the first linkage 212. A slot 2131 is formed along a lengthwise direction of the second linkage 213. The fastening member 2121 is inserted into the slot 2131 at a specific position to fix the relative position of the first linkage 212 and the second linkage 213. Thus, the length of the femur module 21 can be adjusted to meet requirements of different users. As shown in FIG. 3, the proximal first linkage 212 includes the fastening members 2121, and the distal second linkage 213 has the slot 2131. In other embodiments, a contrary design is that a proximal linkage may have a slot and a distal linkage may include fastening member(s). It is only required that the length of the femur module 21 should be adjustable and the linkages can be fixed to each other. The number of the fastening member(s) is not limited for all applications.

The thigh belt 214 is fixed to the first linkage 212 or the second linkage 213. Two ends of the thigh belt 214 have corresponding connection members (not shown) by means of, e.g. buckling or hook-and-loop fastening. The two ends are connected together to go around the thigh 94 of the user to position the femur module 21 at the lateral side of the thigh 94 of the user. By disconnecting or connecting the two ends of the thigh belt 214, the user can wear or remove the femur module 21 conveniently, and also adjust the tightness of the thigh belt 214 easily so as to keep the user in comfort. According to the present invention, the number of the thigh belt(s) 214 is not limited, but must actually bind the femur module 21 to the lateral side of the thigh 94.

Comparing the exoskeleton systems, the conventional exoskeleton system places long brace(s) at one side or two sides of the thigh. It can not fit the muscle extrusion of the thigh for a specific pose (e.g. squatting or sitting). Otherwise, for reserving space for the muscle extrusion, the exoskeleton system in normal use and the human body are spaced apart so that much space is required. On the contrary, by means of the above-described curved linkages 212 and 213 and the thigh belt 214 of the present invention, the curvature of the femur module 21 substantially fits the muscle extrusion so that the femur module 21 is close to the thigh 94, regardless of squatting, sitting or standing. The femur module 21 can be put inside the pants if the user wants to hide the exoskeleton system. It is to be noted that the present invention is not limited to this embodiment, and the user may still use the femur module 21 outside the pants.

In addition, a hip joint connector 215 is optionally disposed between the femur module connector 211 and the first linkage 212. The hip joint connector 215 has one degree of freedom (DOF) to allow the hip joint 93 of the user to perform flexion and extension along the sagittal plane. In another embodiment, the hip joint connector 215 has two degrees of freedom to allow the hip joint 93 of the user to further perform abduction and adduction along the coronal plane. In a further embodiment, the hip joint connector 215 has three degrees of freedom to allow the hip joint 93 of the user to further perform medial rotation and lateral rotation along the transverse plane. The hip joint connector 215 is preferably a ball joint.

Figure 5:
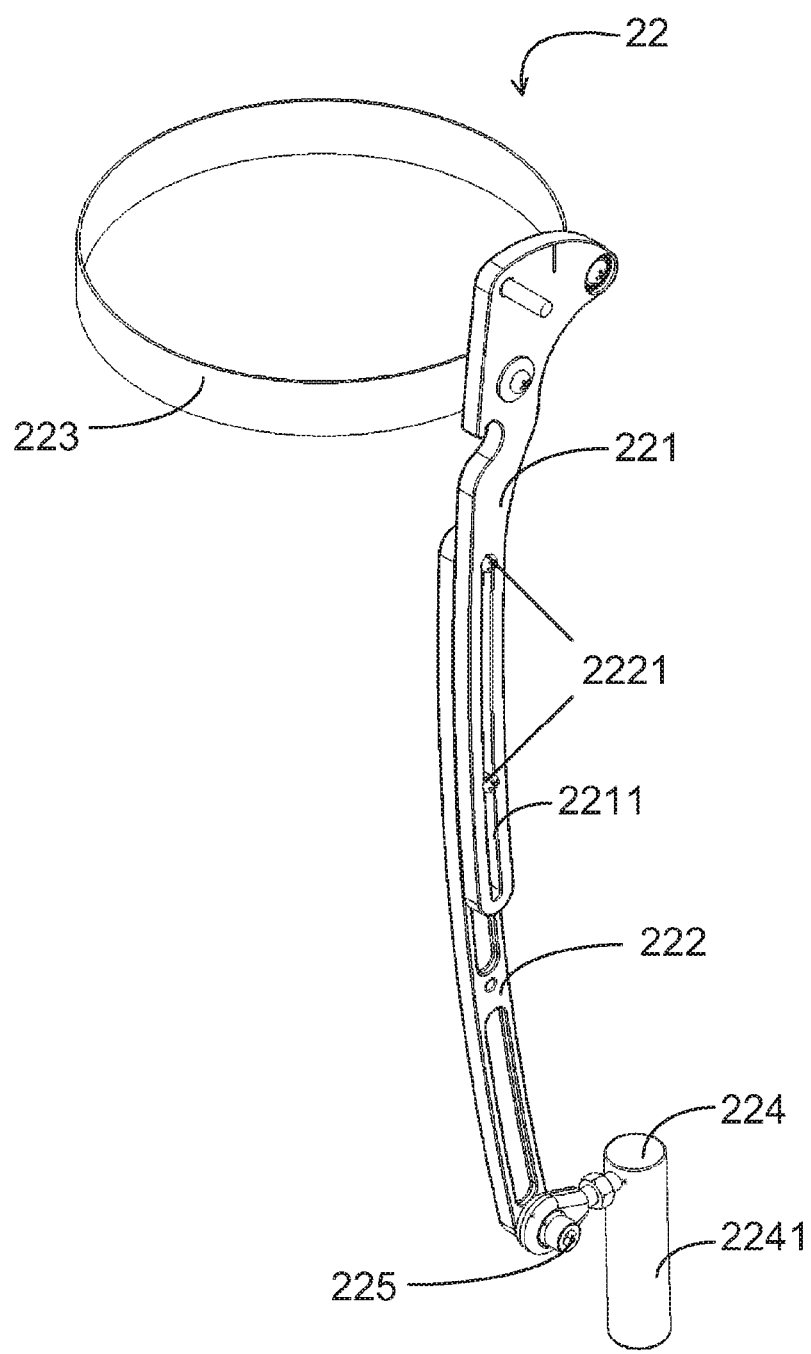
FIG. 5 is a schematic diagram illustrating the tibia module of FIG. 1.

Please refer to FIG. 5, a schematic diagram illustrating the tibia module of FIG. 1. The tibia module 22 includes a third linkage 221, a fourth linkage 222, a shank belt 223 and a tibia module connector 224.

The third linkage 221 and the fourth linkage 222 of the tibia module 22 have the same curvature fitting the shank 96 of the user. A slot 2211 is formed along a lengthwise direction of the third linkage 221. At least one fastening member 2221, e.g. screw, is provided on the fourth linkage 222 along a lengthwise direction of the fourth linkage 222. The fastening member 2221 is inserted into the slot 2221 at a specific position to fix the relative position of the third linkage 221 and the fourth linkage 222. Thus, the length of the tibia module 22 can be adjusted to meet requirements of different users. As shown in FIG. 5, the proximal third linkage 221 has a slot 2211, and the distal fourth linkage 222 includes the fastening members 2221. In other embodiments, a contrary design is that a proximal linkage may include fastening member(s) and a distal linkage may have a slot. It is only required that the length of the tibia module 22 should be adjustable and the linkages can be fixed to each other. The number of the fastening member(s) is not limited for all applications.

The curvature of the linkages 221 and 222 of the tibia module 22 may be identical to the curvature of the linkages 212 and 213 of the femur module 21 to reduce the molds for manufacturing the linkages. For example, one mold is used to manufacture the linkage 212 (proximal femur linkage)

and the linkage 222 (distal tibia linkage), and the other mold is used to manufacture the linkage 213 (distal femur linkage) and the linkage 221 (proximal tibia linkage). The production cost of the portable human exoskeleton system 1 according to the present invention can be reduced. It is to be noted that the present invention is not limited to the embodiment. The applications involving two different curvatures are still included within the scope of the present invention.

The shank belt 223 is fixed to the third linkage 221 or the fourth linkage 222. Two ends of the shank belt 223 have corresponding connection members (not shown) by means of, e.g. buckling or hook-and-loop fastening. The two ends are connected together to go around the shank 96 of the user to position the tibia module 22 at the lateral side of the shank 96 of the user. By disconnecting or connecting the two ends of the shank belt 223, the user can wear or remove the tibia module 22 conveniently, and also adjust the tightness of the shank belt 223 easily so as to keep the user in comfort. According to the present invention, the number of the thigh belt(s) 223 is not limited, but must actually bind the tibia module 22 to the lateral side of the shank 96.

Comparing the exoskeleton systems, the conventional exoskeleton system places long brace(s) at one side or two sides of the shank. It can not fit the muscle extrusion of the shank for a specific pose (e.g. squatting or sitting). Otherwise, for reserving space for the muscle extrusion, the exoskeleton system in normal use and the human body are spaced apart so that much space is required. On the contrary, by means of the above-described curved linkages 221 and 222 and the shank belt 223 of the present invention, the curvature of the tibia module 22 substantially fits the muscle extrusion so that the tibia module 22 is close to the shank 96, regardless of squatting, sitting or standing. The tibia module 22 can be put inside the pants if the user wants to hide the exoskeleton system. It is to be noted that the present invention is not limited to this embodiment, and the user may still use the tibia module 22 outside the pants.

The tibia module connector 224 is disposed at the distal end of the tibia module 22 and has a second coupled part 2241 to be coupled to the foot module 30. The coupling between the second coupled part 2241 and the foot module 30 will be described later.

In addition, an ankle joint connector 225 is optionally disposed between the tibia module connector 224 and the fourth linkage 222. The ankle joint connector 225 has one degree of freedom to allow the ankle joint 97 of the user to perform flexion/plantarflexion and extension/dorsiflexion along the sagittal plane. In another embodiment, the ankle joint connector 225 has two degrees of freedom to allow the ankle joint 97 of the user to further perform abduction/eversion and adduction/inversion along the coronal plane. In a further embodiment, the ankle joint connector 225 has three degrees of freedom to allow the ankle joint 97 of the user to further perform medial rotation and lateral rotation along the transverse plane. The ankle joint connector 225 is preferably a ball joint.

Figure 6:
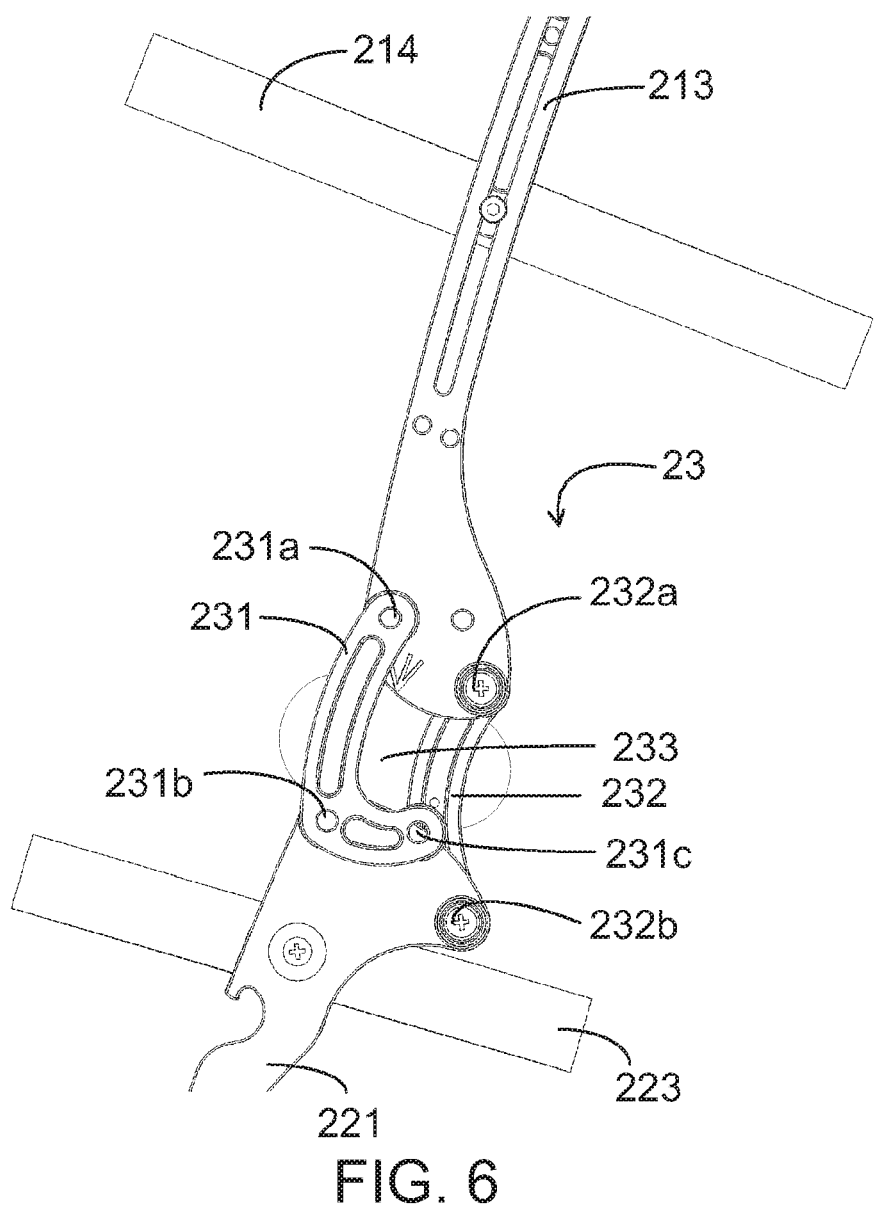
FIG. 6 is a schematic diagram illustrating the knee joint component of FIG. 1.
Figure 7:
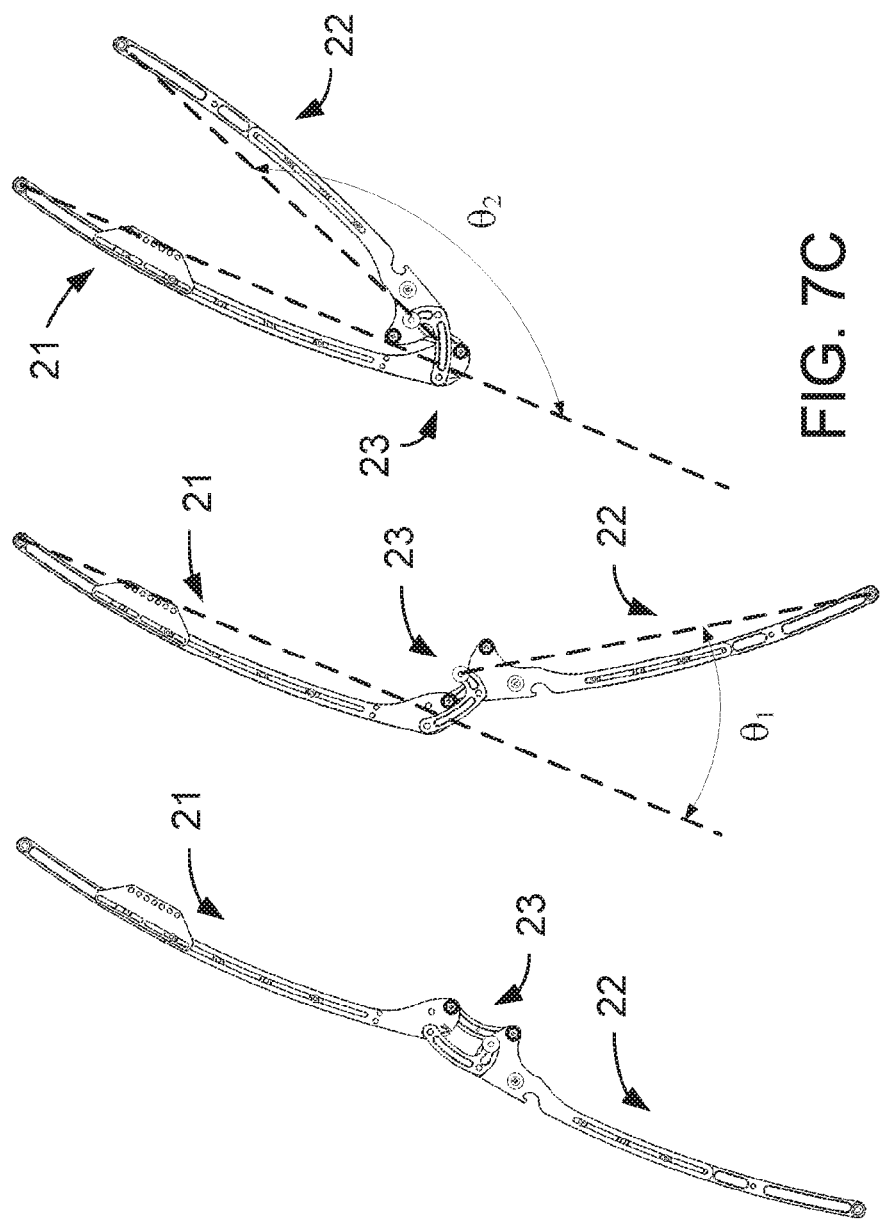
FIGS. 7A-7C are schematic diagrams showing relative positions of the femur module, the tibia module and the knee joint component in an extension mode and a flexion mode.

Please refer to FIG. 6, a schematic diagram illustrating the knee joint component of FIG. 1. The knee joint component 23 is pivotally coupled to the femur module 21 and the tibia module 22. More specifically, the knee joint component 23 is pivotally coupled between the second linkage 213 and the third linkage 221 and includes at least two short linkages 231 and 232 with different lengths. The short linkage 231 is jointed to the second linkage 213 and the third linkage 221 at pivot joints 231a, 231b and 231c. The short linkage 232 is jointed to the second linkage 213 and the third linkage 221 at pivot joints 232a and 232b. The tibia module 22 together with the femur module 21 is allowed to flex or extend. In this embodiment, the short linkage 231 is an L-shape linkage, but is not limited to this. A bar linkage is also applicable. The relative positions of the femur module 21, the tibia module 22 and the knee joint component 23 are shown in FIGS. 7A, 7B and 7C. FIG. 7A shows a full extension mode, and FIGS. 7B and 7C show flexion modes. The flexion angle in FIG. 7C is greater than that in FIG. 7B, i.e. $\theta_2 > \theta_1$.

When the user is walking, a force is usually exerted on the medial side of the leg. Therefore, the space between the femur and the tibia near the median becomes smaller, and the bones near the contact point between the femur and the tibia are easily worn excessively to cause osteoarthritis. A soft pad 233 is optionally disposed at the medial side of the knee joint component 23. The soft pad 233 is in contact with the lateral side of the knee joint 95 of the user to generate a medial force. The medial force and the thigh belt 214 result in an upward force to the medial side of the thigh 94 of the user, and the medial force and the shank belt 223 result in a downward force to the shank 96 of the user. An abduction torque is formed to separate the femur and the tibia by a space about 2-3 mm. It helps to release the pressure at the medial side of the knee joint 95 of the user to avoid the wear of the bones.

Figure 8:
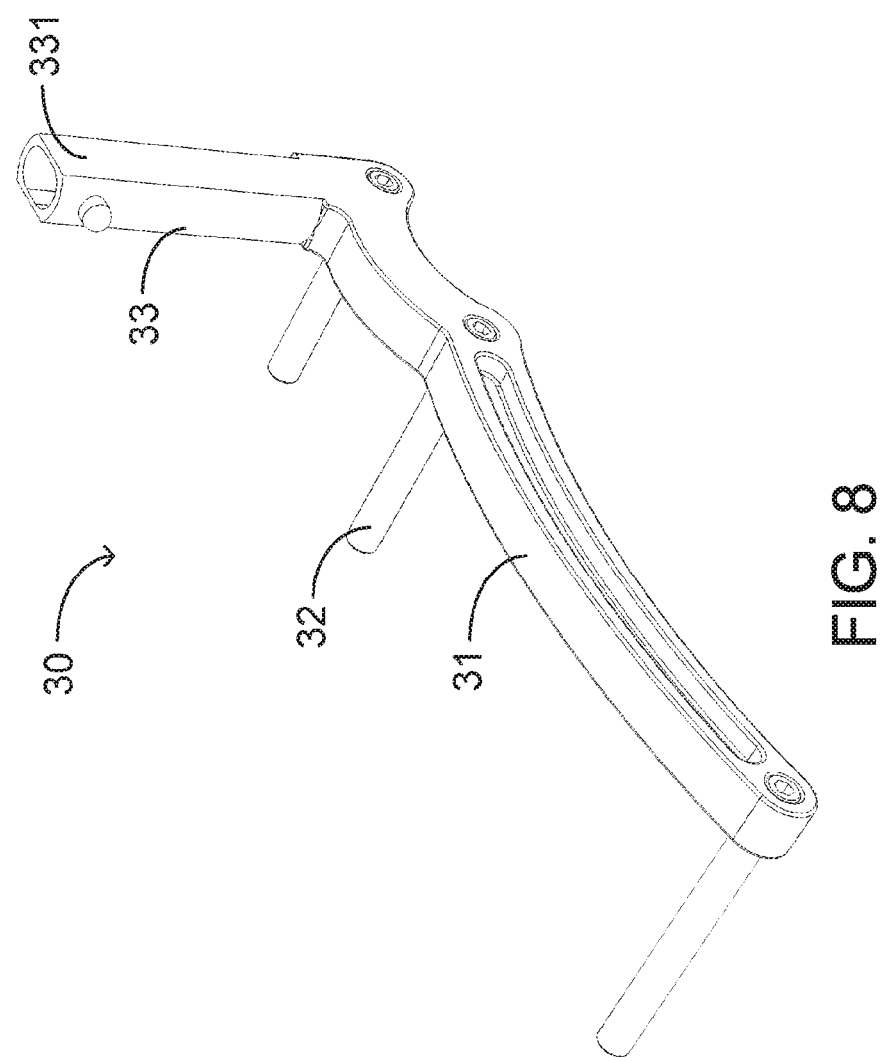
FIG. 8 is a schematic diagram illustrating the foot module of FIG. 1.

Please refer to FIG. 8, a schematic diagram illustrating the foot module of FIG. 1. The foot module 30 includes a foot frame 31, a support element and a foot module connector 33. The foot frame 31 extends along a lengthwise direction of the foot 98 of the user, and the length of the foot frame 31 is not longer than 1.5 times of the length of the foot 98. The foot frame 31 is positioned at the lateral side of the foot 98 of the user to maintain the stability of itself along the sagittal plane of the human body. One end of the support element 32 is connected to the foot frame 31 and the other end extends along a medial direction of the foot 98 of the user, i.e. substantially perpendicular to the foot frame 31. The length of the support element 32 is not longer than 1.5 time of the width of the foot 98 to maintain the stability of itself along the coronal plane of the human body. The support element 32 is inserted into a sole or an insole of a shoe worn by the user. As shown in FIG. 8, three support elements 32 are respectively connected to a front portion, a middle portion and a rear portion of the foot frame 31, but the number of the support element(s) 32 is not limited to the embodiment. If there is only one support element 32, it is preferable disposed at the rear portion of the foot frame 31. Although the rod support element 32 is shown in the drawing, a block support element or a plate support element is also applicable.

The foot module connector 33 includes a second coupling part 331 to be attached to the second coupled part 2241 of the tibia module connector 224 to from detachable coupling. The coupling is similar to that between the pelvis module connector 12 and the femur module connector 211 as described above. One or multiple holes (not shown) are disposed on the second coupling part 331 of the foot module connector 33. One or multiple corresponding buttons or other elastic members (not shown) are disposed on the second coupled part 2241 of the tibia module connector 224. When the second coupled part 2241 is inserted into the second coupling part 331, the button protrudes from the hole so that the second coupled part 2241 is fixed in the second coupling part 331. Thus, the tibia module 22 is coupled to the foot module 30. To detach the second coupling part 331 from the second coupled part 2241, the user presses the button and pulls the second coupled part 2241 upwards (or toward the front or the lateral side according to the design for specific user). Then, the tibia module 22 and the foot module 30 are separated. The present invention does not limit the detachable coupling to the embodiment. For example, the detachable coupling may be achieved by a tenon and mortise structure, a magnetic element, a hook-and-loop fastener, a buckle or a combination thereof. Hence, the present invention provides a quick and convenient way of detachment and attachment. The user can easily finish the detachment or attachment by himself or herself, even by single hand. For example, the left tibia module 22 can be attached to or detached from the foot module 30 only by right hand operation.

The present invention provides a detachable leg module 20 (including the femur module 21, the tibia module 22 and the knee joint component 23) which is easy to disassemble and carry. When the user uses the portable human exoskeleton system 1 outside but the portable human exoskeleton system 1 is not necessary for a certain period, e.g. sitting, the user can remove the leg module 20 and leave the pelvis module 10 and the foot module 30 worn. So that the user can move freely. The removed leg module 20 is folded as the flexion mode, and the small size is advantageous to carrying. On the contrary, while using the conventional exoskeleton system, the user has to put on or take off the entire system. It is not only inconvenient, but also taking up much space. Furthermore, due to the detachable coupling between the foot module 30 and the leg module 20, the user may have several foot modules 30 working with his or her favorite shoes according to demands. The manufacturer inserts the support elements 32 of the foot modules 30 into the soles or insoles of the shoes in advance. The user may select proper shoes for specific occasion without adapting the present system for the user for every different selection because the selected shoe(s) has been adapted in advance. The present exoskeleton system is much convenient than the conventional exoskeleton system.

Figure 9:
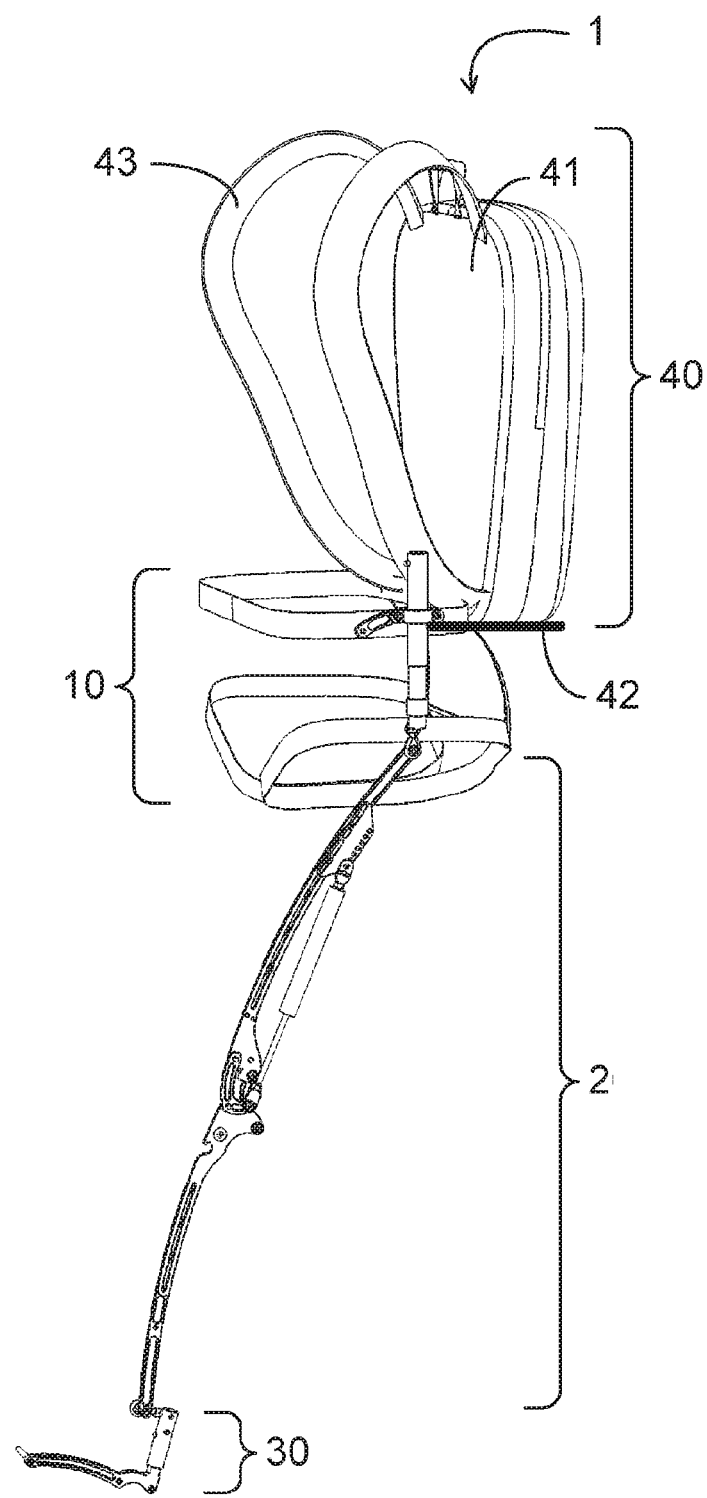
FIG. 9 is a schematic diagram illustrating a portable human exoskeleton system according to another embodiment of the present invention.

The portable skeleton system 1 of the invention optionally includes a load-carrying module 40 (FIG. 9). It is connected to the pelvis module connector 12 of the pelvis module 10. The load-carrying module 40 includes a carry pack 41, a support member 42 and a strap 43. The carry pack 41 can contain an object to be carried. The support member 42 is connected to the pelvis module connector 12 and supports the carry pack 41. The strap 43 is connected to the carry pack 41 and worn over the arm of the user to fix the position of the carry pack 41. According to the design, the weight above the hip 92 (including the load) is exerted on the pelvis module 10, transferred from the pelvis module 10 to the leg module 20, than transferred to the foot module 30 and finally transferred to the ground. No weight or less weight is exerted on any portion of the human body, especially the weaker knee joint 95 or ankle 97.

Figure 10B:
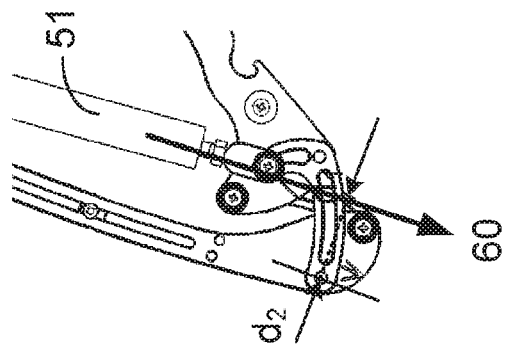
FIG. 10A and FIG. 10B are schematic diagrams showing that the force transmission device controls the knee joint component according to an embodiment of the present invention.
Figure 10A:
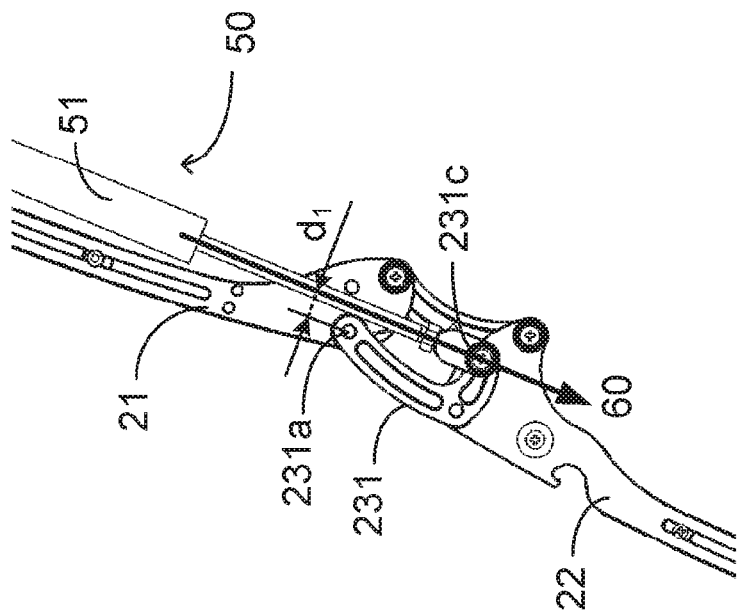

To reduce the load of the knee joint 95 in some poses, the present invention provides a force transmission device 50 to control the knee joint component 23 and/or the leg module 20. Please refer to FIG. 10A and FIG. 10B. The force transmission device 50 includes a moment arm-adjusting structure and a driving element. In this embodiment, the moment arm-adjusting structure is an L-shape linkage 231 having a pivot joint 231a pivotally coupled to the distal end of the femur module 21. The driving element is a cylinder 51 wherein one end is connected to the pelvis module 10 or the femur module 21, and the other end is connected to an input force joint 231c of the L-shape linkage 231 or the tibia module 22. The cylinder 51 provides a pushing force 60 to urge the femur module 21 and the tibia module 22 toward the extension mode. In FIG. 10A, the pushing force 60 corresponds to an effective moment arm $d_1$ about the pivot joint 231a. In FIG. 10B, the pushing force 60 corresponds to an effective moment arm $d_2$ about the pivotal joint 231a. In a preferred embodiment, a greater flexion angle corresponds to a greater effective moment arm to provide a greater extension moment to urge the femur module 21 and the tibia module 22 to return to the extension mode quickly.

The design of the force transmission device 50 has many advantages. For example, standing stability is improved. Furthermore, it is not too hard for the user to change the poses from squatting to standing by taking advantage of the extension moment. When the user wants to sit or squat, the speed of sitting or squatting is lowered to prevent from impact on the knee joint 95. Furthermore, the extension moment can reduce shocks during downstairs or downhill motion.

The user can manually control the inflation, deflation or pressure-holding of the cylinder 51 to control the knee joint component 23 and the leg module 20. Therefore, a manual valve (not shown) is provided to increase the flexibility of the application. For example, when the user falls down, and the cylinder 51 continues to provide the pushing force 60 to the tibia module 22 to force the leg of the user to extend, the user can not stand up successfully. At this time, the user can manually deflate the cylinder 51 to stop the pushing force 60 to the tibia module 22. After the user keeps his or her feet, the cylinder 51 recovers to pressure-holding.

Please refer to FIG. 11A and FIG. 11B, showing another force transmission device 50 including a moment arm-adjusting structure and a driving element 53. In this embodiment, the moment arm-adjusting structure is a cam 52 having a pivot joint 52a pivotally coupled to the distal end of the femur module 21. The driving element 53 is a spring or a combination of a spring and a cable wherein one end is connected to the pelvis module 10 or the femur module 21, and the other end is connected to an input force joint 52b of the cam 52 or the tibia module 22. The driving element 53 provides a pulling force 62 to urge the femur module 21 and the tibia module 22 toward the extension mode. If the driving element 53 is connected to the input force joint 52b of the cam 52, a hook structure 54 is further provided to be pivotally coupled to the cam 52 to hook a notch 226 on the tibia module 22 to transfer the pulling force 62 to the tibia module 22. In FIG. 11A, the pulling force 62 corresponds to an effective moment arm $d_1$ about the pivot joint 52a. In FIG. 11B, the pulling force 62 corresponds to an effective moment arm $d_2$ about the pivot joint 52a. In a preferred embodiment, a greater flexion angle corresponds to a greater effective moment arm to provide a greater extension moment to urge the femur module 21 and the tibia module 22 to return to the extension mode quickly. This design uses a passive member such as spring or elastic member to transfer energy. Therefore, no power generation device such as battery is required. The overall weight of the human exoskeleton system 1 and the production cost are reduced.

The design of the force transmission device 50 has many advantages. For example, standing stability is improved. Furthermore, it is not too hard for the user to change the poses from squatting to standing by taking advantage of the extension moment. When the user wants to sit or squat, the speed of sitting or squatting is lowered to prevent from impact on the knee joint 95. Furthermore, the extension moment can reduce shocks during downstairs or downhill motion.

As described above, the force transmission of the pulling force 62 to the tibia module 22 may be undesired on a specific occasion. For example, when the user falls down, and the driving element 53 continues to provide the pulling force 62 to the tibia module 22 to force the leg of the user to extend, the user can not stand up successfully. At this time, the user can detach the hook structure 54 from the notch 226 on the tibia module 22 to stop the pulling force 62 pulling the tibia module 22. After the user keeps his or her feet, the hook structure 54 is allowed to hook the notch 226 again to provide the pulling force 62 to recover the extension function.

In conclusion, the portable human exoskeleton system of the present invention involves many specific designs. It can be easily disassembled and carried, and can be worn inside attire without affecting appearance of the user. In addition, the extension moment and/or the soft pad can properly protect the knee joint. The length of the leg module may be easily adjusted. Therefore, the present invention rich in practicability.

Although the present invention has been disclosed in the above preferred embodiments, the present invention is not limited to these. Modifications and adjustments thereto made by a person skilled in the arts are included within the spirit and scope of the present invention. Therefore, the present invention should be defined according to the appended claims.

What is claimed is:

1. A portable human exoskeleton system, comprising:
    a pelvis module (10), comprising:
        a bendable module (11), being configured to be wrapped around a body of a user for being configured to fix the pelvis module (10) to a hip (92) of the user and comprising a waist belt (111), two groin belts (112), two holding belts (113), and a tension belt (114), the waist belt (111) being connected to a proximal end of the pelvis module connector (12) and configured to be worn around a waist (91) of the user, each of the two groin belts (112) being connected to a distal end of the pelvis module (10), and being configured to be along a lateral side of a pelvis (93), a groin and an ischium of the user, and back to the lateral side of the pelvis (93), wherein the waist belt (111) and the two groin belts (112) are annular members with fixed shapes, the two holding belts (113) being connected between the waist belt (111) and the two groin belts (112) in order to prevent the groin belts (112) from sliding downwards, the tension belt (114) being connected between the two groin belts (112) behind the hip (92) for preventing the two groin belts (112) from sliding along two thighs (94) of the user or limiting sliding ranges; and
        a pelvis module connector (12), being connected to the bendable module (11) and configured to be positioned near a lateral side of a hip joint (93) of the user, the waist belt (111) and the groin belt (112) being respectively connected to a proximal end and a distal end of the pelvis module connector (12);
    a foot module (30), being configured to be worn on a foot (98) of the user and having a foot frame (31), at least one support element (32) and a foot module connector (33), the foot frame (31) being configured to be extended along a lengthwise direction of the foot (98) of the user and configured to be positioned at a lateral side of the foot (98) of the user, the support element (32) having a first end and a second end, the first end being connected to the foot frame (31) and the second end being configured to be extended along a medial direction of the foot (98) of the user; and
    a leg module (20), being configured to be positioned at a lateral side of a leg of the user, comprising:
        a femur module (21), being detachably coupled to the pelvis module connector (12) and comprising a first linkage (212) having a first curvature configured to be fit a thigh (94) of the user, wherein at least one fastening member (2121) is provided on the first linkage (212) along a lengthwise direction of the first linkage (212); and a second linkage (213) having the first curvature and comprising a slot (2131) formed along a lengthwise direction of the second linkage (213), the fastening member (2121) of the first linkage (212) being inserted into the slot (2131) of the second linkage (213) at a specific position to fix a relative position of the first linkage (212) and the second linkage (213);
        a tibia module (22), being detachably coupled to the foot module connector (33), the foot module connector (33) being connected to one end of the foot frame (31) and comprising a second coupling part (331), the tibia module (22) comprising a third linkage (221), a fourth linkage (222), a shank belt (223), and a tibia module connector (224), the tibia module connector (224) being at a distal end of the tibia module (22), a second coupled part (2241) of the tibia module connector (224) being attached to the second coupling part (331), wherein the tibia module connector (224) and the foot module connector (33) form detachable coupling, the tibia module (22) being coupled to the foot module (30) when the second coupled part (2241) is attached to the second coupling part (331), the tibia module (22) being separated from the foot module (30) when the second coupled part (2241) is detached from the second coupling part (331), the third linkage (221) having a second curvature configured to be fit a shank (96) of the user and comprising a slot (2211) formed along a lengthwise direction of the third linkage (221), the fourth linkage (222) having the second curvature wherein at least one fastening member (2221) is provided on the fourth linkage (222) along a lengthwise direction of the fourth linkage (222), the fastening member (2221) of the fourth linkage (222) being inserted into the slot (2211) of the third linkage (221) at a specific position to fix relative positions of the third linkage (221) and the fourth linkage (222), the shank belt (223) being fixed to the third linkage (221) or the fourth linkage (222), the shank belt (223) being configured to be worn around the shank (96) of the user by connecting two ends of the shank belt (223) together; and
        a knee joint component (23), being pivotally coupled between the second linkage (213) and the third linkage (221) and having at least two linkages (231, 232) with different lengths, each of the linkages (231, 232) being pivotally coupled to the femur module (21) and the tibia module (22) at pivot joints (231*a*, 231*b*, 231*c*, 232*a*, 232*b*);
    wherein weight above the hip (92) of the user is exerted on the pelvis module (10), transferred from the pelvis module (10) to the leg module (20), and then transferred to the foot module (30).

2. The portable human exoskeleton system according to claim 1, wherein
    the pelvis module connector (12) comprises a first coupling part (121);
    the femur module (21) comprises a femur module connector (211) at a proximal end of the femur module (21), and the femur module connector (211) comprises a first coupled part (2111) attached to the first coupling part (121);

wherein the femur module connector (211) and the pelvis module connector (12) form a detachable coupling, the femur module (21) being coupled to the pelvis module (10) when the first coupled part (2111) is attached to the first coupling part (121), the femur module (21) being separated from the pelvis module (10) when the first coupled part (2111) is detached from the first coupling part (121).

3. The portable human exoskeleton system according to claim 1, wherein the support element (32) is inserted into a sole or an insole of a shoe configured to be worn by the user.

4. The portable human exoskeleton system according to claim 1, wherein the femur module (21) comprises a thigh belt (214) fixed to the first linkage (212) or the second linkage (213), the thigh belt (214) being configured to be worn around the thigh (94) of the user by connecting two ends of the thigh belt (214) together.

5. The portable human exoskeleton system according to claim 1, wherein the first curvature is equal to the second curvature.

6. The portable human exoskeleton system according to claim 1, further comprising a force transmission device (50), the force transmission device (50) comprising:
- a moment arm-adjusting structure having a pivot joint (231) pivotally coupled to a distal end of the femur module (21); and
- a driving element (51 or 53) having a first end and a second end, the first end of the driving element (51 or 53) being connected to the pelvis module (10) or the femur module (21), the second end of the driving element (51 or 53) being connected to an input force joint (231c) of the moment arm-adjusting structure or the tibia module (22), the driving element (51) providing a force to urge the femur module (21) and the tibia module (22) toward an extension mode, the force corresponding to a first effective moment arm about the pivot joint (231a) when the femur module (21) and the tibia module (22) have a first flexion angle, the force corresponding to a second effective moment arm about the pivot joint (231a) when the femur module (21) and the tibia module (22) have a second flexion angle smaller than the first flexion angle, wherein the first effective moment arm is greater than the second effective moment arm.

7. The portable human exoskeleton system according to claim 6, wherein the driving element is connected to the input force joint of the moment arm-adjusting structure, and the force transmission device further comprises a hook structure pivotally coupled to the moment arm-adjusting structure, the force being applied to the tibia module when the hook structure hooks a notch on the tibia module, the force being not applied to the tibia module when the hook structure is detached from the notch.

8. The portable human exoskeleton system according to claim 1, further comprising a load-carrying module connected to the pelvis module connector of the pelvis module.

9. The portable human exoskeleton system according to claim 1, further comprising:
- the groin belt (112) fixed to the femur module (21);
- the shank belt (223) fixed to the tibia module (22); and
- a soft pad (233), being fixed to a medial side of the knee joint component (23) and configured to be in contact with a lateral side of a knee joint (95) of the user to provide a medial force, wherein the groin belt (112), the shank belt (223) and the soft pad (233) collectively provide an abduction moment to the knee joint (95).

\* \* \* \* \*